US009505985B2

(12) United States Patent
Court et al.

(10) Patent No.: US 9,505,985 B2
(45) Date of Patent: Nov. 29, 2016

(54) METHOD FOR CONVERTING LIGNOCELLULOSIC MATERIALS INTO USEFUL CHEMICALS

(75) Inventors: Gregory Ross Court, East Melbourne (AU); Christopher Howard Lawrence, Templestowe (AU); Warwick Douglas Raverty, Viewbank (AU); Anthony James Duncan, Brighton (AU)

(73) Assignee: CIRCA GROUP PTY LTD (AU)

( * ) Notice: Subject to any disclaimer, the term of this patent is extended or adjusted under 35 U.S.C. 154(b) by 989 days.

(21) Appl. No.: 13/381,176

(22) PCT Filed: Jun. 29, 2010

(86) PCT No.: PCT/AU2010/000811
§ 371 (c)(1),
(2), (4) Date: Dec. 28, 2011

(87) PCT Pub. No.: WO2011/000030
PCT Pub. Date: Jan. 6, 2011

(65) Prior Publication Data
US 2012/0111714 A1    May 10, 2012

(30) Foreign Application Priority Data
Jul. 1, 2009 (AU) ................................ 2009903060

(51) Int. Cl.
*C10L 1/18* (2006.01)
*C10G 1/08* (2006.01)
(Continued)

(52) U.S. Cl.
CPC .............. *C10G 1/083* (2013.01); *C07C 51/09* (2013.01); *C10B 7/10* (2013.01); *C10B 53/02* (2013.01);
(Continued)

(58) Field of Classification Search
CPC ............ C10G 1/00; C10G 1/02; C10G 1/08; C10L 1/18
See application file for complete search history.

(56) References Cited

U.S. PATENT DOCUMENTS 4,316,747 A * 2/1982 Rugg et al. .................... 127/37
5,536,325 A * 7/1996 Brink .............................. 127/43
(Continued)

FOREIGN PATENT DOCUMENTS

CA        2260570        7/2000
CA        2260570 A1 *   7/2000
(Continued)

OTHER PUBLICATIONS

Kawamoto, H. et al. "Catalytic Pyrolysis of Cellulose in Sulfolane with Some Acidic Catalysts". J Wood Sci. 2007, vol. 53:127, p. 127-133.*
(Continued)

*Primary Examiner* — In Suk Bullock
*Assistant Examiner* — Jonathan Miller
(74) *Attorney, Agent, or Firm* — Galbreath Law Offices, P.C.; John A. Galbreath

(57) ABSTRACT

A method of converting particulate lignocellulosic material to produce volatile organic compounds and char, comprising,
forming a mixture of the particulate lignocellulosic material with a catalyst composition containing polar organic liquid and an acid in the presence or absence of added water,
heating the mixture to a temperature sufficiently high and for a period sufficiently long as to convert a major portion of any remaining solid phase of the mixture to char while agitating the mixture, and
separating volatile organic compounds and the catalyst composition as a gaseous phase from the solid phase.

9 Claims, 3 Drawing Sheets

Figure 1:
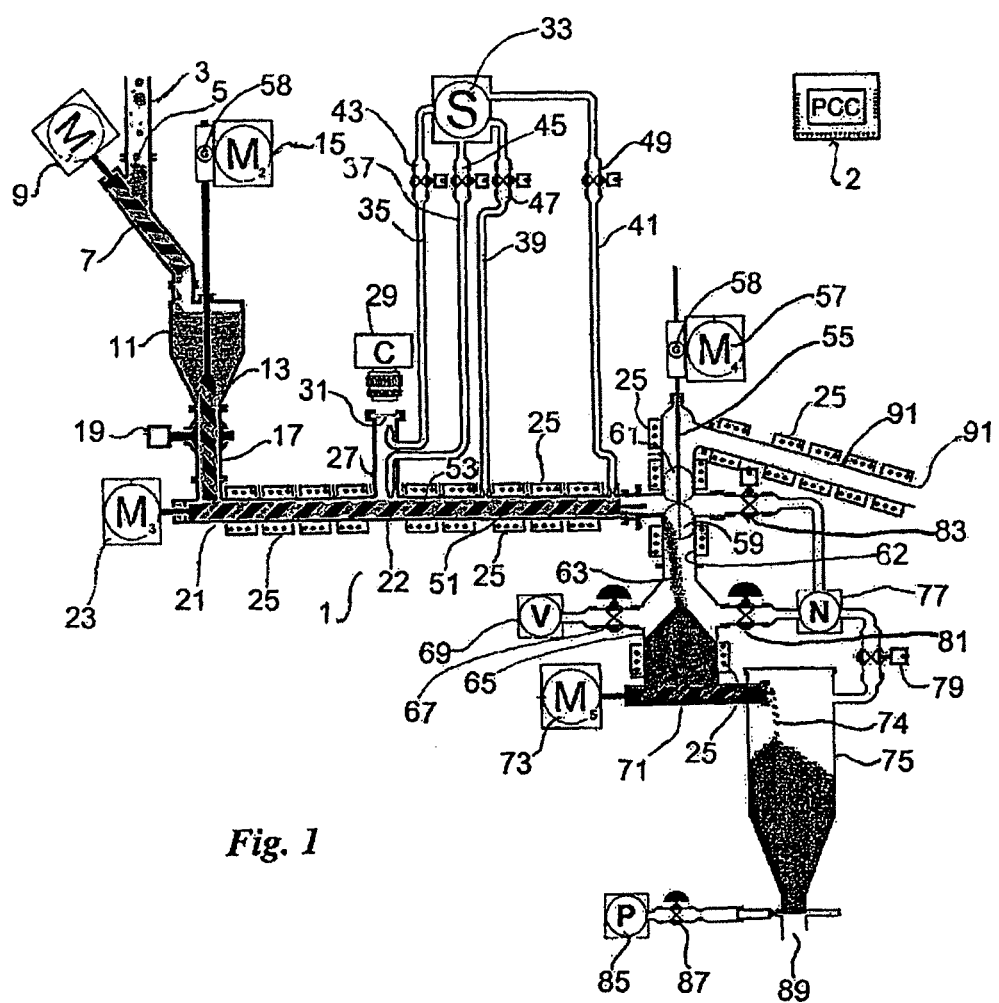

(51) Int. Cl.
  C10B 7/10    (2006.01)
  C10B 53/02   (2006.01)
  C10G 1/02    (2006.01)
  C07C 51/09   (2006.01)
(52) U.S. Cl.
  CPC .............. *C10G 1/02* (2013.01); *C10G 1/086* (2013.01); *C10L 1/18* (2013.01); *C10G 2300/1014* (2013.01); *Y02E 50/14* (2013.01); *Y02P 30/20* (2015.11)

(56) References Cited

U.S. PATENT DOCUMENTS

| | | | | |
|---|---|---|---|---|
| 5,632,863 | A * | 5/1997 | Meador | 201/25 |
| 5,916,780 | A * | 6/1999 | Foody et al. | 435/99 |
| 5,972,118 | A * | 10/1999 | Hester et al. | 127/1 |
| 6,653,517 | B2 * | 11/2003 | Bullock | 585/241 |
| 6,833,485 | B2 * | 12/2004 | Nichols et al. | 585/241 |
| 2002/0072641 | A1 | 6/2002 | Nichols et al. | |
| 2002/0177745 | A1 | 11/2002 | Bullock | |
| 2005/0165262 | A1 | 7/2005 | Nichols et al. | |
| 2008/0072478 | A1 * | 3/2008 | Cooper | 44/606 |
| 2008/0185112 | A1 * | 8/2008 | Argyropoulos | 162/9 |
| 2010/0223839 | A1 * | 9/2010 | Garcia-Perez | C01B 3/34 44/313 |
| 2012/0190062 | A1 | 7/2012 | O'Connor et al. | |

FOREIGN PATENT DOCUMENTS

| | | | |
|---|---|---|---|
| EP | 0 366 138 | | 5/1990 |
| EP | 0366138 | A2 * | 5/1990 |
| WO | 2008/017145 | | 2/2008 |
| WO | 2009/155297 | | 12/2009 |
| WO | WO 2009155297 | A1 * | 12/2009 ........... C07D 307/48 |

OTHER PUBLICATIONS

Bhattacharya et al., "Wood/plastic Copyrolysis in an Auger Reactor: Chemical and Physical Analysis of the Products," Fuel 88, pp. 1251-1260 (2009).
Boon et al., "Structural Studies on Cellulose Pyrolysis and Cellulose Chars by PYMS, PYG-CMS, FTIR, NMR and by Wet Chemical Techniques," Biomass and Bioenergy, vol. 7, Nos. 1-6, pp. 25-32 (1994).
Bridgwater et al., An Overview of Fast Pyrolysis of Biomass, Organic Geochemistry 30, pp. 1479-1493 (1999).
Broido et al., "Yield of 1,6-Anhydro-3,4-Dideoxy-{3-n-glycero-Hex-3-Enopyranos-2-Ulose (Levoglucosenone) on the Acid-catalyzed Pyrolysis of Cellulose and 1,6-Anhydro-{3-o-Glucopyranose Levoglucosan)," Carbohydrate Research 44, pp. 267-274 (1975).
Brown et al., "Pretreatment Processes to Increase Pyrolytic Yield of Levoglucosan from Herbaceous Feedstocks," American Chemical Society, pp. 123-132 (2001).
Chen et al., "Catalytic Effects of Eight Inorganic Additives on Pyrolysis of Pine Wood Sawdust by Microwave Heating," Journal of Analytical and Applied Pyrolysis, pp. 1-29 (2008).
Cullis et al., "The Pyrolysis of Cellulose under Conditions of Rapid Heating," Combustion and Flame 49, pp. 235-248 (1983).
De Wild et al., "Biomass Valorisation by Staged Degasification: A New Pyrolysis-based Conversion Option to Produce Value-added Chemicals From Lignocellulosic Biomass," Journal of Analytical and Applied Pyrolysis 85, pp. 124-133 (2008).
De Wild, "Biomass Pyrolysis for Chemicals," pp. 1-173 (2008).
Dobele et al., "Application of Catalysts for Obtaining 1,6-anhydrosaccharides from Cellulose and Wood by Fast Pyrolysis," Journal of Analytical and Applied Pyrolysis, vol. 74, pp. 401-405 (2005).
Dobele et al., "Cellulose Dehydration and Depolymerization Reactions During Pyrolysis in the Presence of Phosphoric Acid," Journal of Analytical and Applied Pyrolysis 49, pp. 307-317 (1999).

Dobele et al., "Pre-Treatment of Biomass with Phosphoric Acid Prior to Fast Pyrolysis A Promising Method for Obtaining 1,6-anhydrosaccharides in High Yields," Journal of Analytical and Applied Pyrolysis, vols. 68-69, pp. 197-211 (2003).
Dobele et al., "Volatile Products of Catalytic Flash Pyrolysis of Celluloses," Journal of Analytical and Applied Pyrolysis 58-59, pp. 453-463 (2001).
Garcia-Perez et al., "Production and Fuel Properties of Pine Chip Bio-oil/Biodiesel Blends," Energy & Fuels 12, pp. 2363-2372 (2007).
Guirong et al., "Cellulose Decomposition Behavior in Hot-Compressed Aprotic Solvents," Science in China Series B: Chemistry, vol. 51, No. 5, pp. 479-486 (May 2008).
Halpern et al., "Levoglucosenone (1,6-Anhydro-3,4-dideoxy-A8-/1-D-Pyranosen-2-one). A Major Product of the Acid-Catalyzed Pyrolysis of Cellulose and Related Carbohydrates," Journal of Organic Chemistry, vol. 38, No. pp. 204-209 (1973).
Hassan et al., "The Potential Use of Whole-tree Biomass for Bio-oil Fuels," Energy Sources, Part 1 31, pp. 1829-1839 (2009).
Hosoya et al., "Different Pyrolytic Pathways of Levoglucosan in Vapor-and Liquid/Solid-phases," Journal of Analytical and Applied Pyrolysis 83, pp. 64-70 (2008).
Hosoya et al., "Thermal Stabilization of Levoglucosan in Aromatic Substances," Carbohydrate Research 341, pp. 2293-2297 (2006).
Ingram et al., "Pyrolysis of Wood and Bark in an Auger Reactor: Physical Properties and Chemical Analysis of the Produced Bio-oils," Energy & Fuels 22, pp. 614-625 (2008).
Kadota et al., "Lipase-Mediated Synthesis of Both Enantiomers of Levoglucosenone from Acrolein Dimer," Adv. Synth. Catal.,vol. 343, No. 6-7 (2001).
Kawamoto and Saka, "Heterogeneity in Cellulose Pyrolysis Indicated from the Pyrolysis in Sulfolane," Journal of Analytical and Applied Pyrolysis 76, pp. 280-284 (2006).
Kawamoto and Saka, "Pyrolysis Mechanism of Woody Biomass Relating to Product Selectivity," American Chemical Society, pp. 363-376 (2007).
Kawamoto and Saka, "Wood Pyrolysis Mechanism on Molecular Basis for Selective Conversion into Liquid Fuels," Kyoto University 21COE (2006).
Kawamoto and Sako, "Wood Pyrolysis Mechanism on Molecular Basis for Selective Conversion into Liquid Fuels," The 2nd Joint International Conference on Sustainable Energy and Environment (SEE 2006) C-033 (O), Bangkok, Thailand (Nov. 2006).
Kawamoto et al., "Catalytic Pyrolysis of Cellulose in Sulfolane with Some Acidic Catalysts," The Japan Wood Research Society, vol. 53, pp. 127-133 (Dec. 2, 2006).
Kawamoto et al., "Pyrolysis Behavior of Levoglucosan as an Intermediate in Cellulose Pyrolysis: Polymerization into Polysaccharide as a Key Reaction to Carbonized Product Formation," Journal of Wood Sciences 49, pp. 469-473 (2003).
Kawamoto et al., "Stable Complex Formation with Boric Acid in Pyrolysis of Levoglucosan in Acidic Media," Journal of Analytical and Applied Pyrolysis 82, pp. 78-82 (2008).
Kawamoto et al., "Thermochemical Conversion of Cellulose in Polar Solvent (Sulfolane) into Levoglucosan and Other Low Molecular-Weight Substances," Journal of Analytical and Applied Pyrolysis, vol. 70, pp. 303-313 (2003).
Kwon et al., "Rapid-Cooling, Continuous-Feed Pyrolyzer for Biomass Processing Preparation of Levoglucosan from Cellulose and Starch," Journal of Analytical and Applied Pyrolysis 80, pp. 1-5 (2007).
Lakshmanan et al., "Production of Levoglucosan by Pyrolysis of Carbohydrates," I & EC Product Research and Development, vol. 8, No. 3, pp. 261-267 (Sep. 1969).
Lin et al., "Coal Desulfurization by Mild Pyrolysis in a Dual-Auger Coal Feeder," Fuel Processing Technology 53, pp. 15-29 (1997).
Marshall, "An Improved Preparation of Levoglucosenone from Cellulose," Master Abstracts International, vol. 46, No. 5 (2008).
Mok et al., "Fast Pyrolysis (Ultrapyrolysis) of Cellulose and Wood Components," Journal of Analytical and Applied Pyrolysis 8, pp. 391-400 (1985).

(56) References Cited

OTHER PUBLICATIONS

Nowakowski et al., "Phosphorus Catalysis in the Pyrolysis Behavior of Biomass," Journal of Analytical and Applied Pyrolysis 83, 00. 197-204 (2008).
Olazar et al., "Catalyst Effect on the Composition of Tire Pyrolysis Products," Energy & Fuels 22, pp. 2909-2916 (2008).
Pan and Richards, "Influence of Metal Ions on Volatile Products of Pyrolysis of Wood," Journal of Analytical and Applied Pyrolysis 16, pp. 117-126 (1989).
Ponder and Richards, "A Review of Some Recent Studies on Mechanisms of Pyrolysis of Polysaccarides," Biomass and Bioenergy, vol. 7, Nos. 1-6, pp. 1-24 (1994).
Radlein et al., "Fast Pyrolysis of Natural Polysaccharides as a Potential Industrial Process," Journal of Analytical and Applied Pyrolysis 19, pp. 41-63 (1991).
Richards et al., "Influence of Sodium Chloride on Volatile Products Formed by Pyrolysis of Cellulose: Identification of Hydroxybenzenes and 1-hydroxy-2-propanone as Major Products," Carbohydrate Research 117, pp. 322-327 (1983).
Sanders et al., "A Model that Distinguishes the Pyrolysis of Dglucose, D-fructose, and Sucrose From That of Cellulose. Application to the Understanding of Cigarette Smoke Formation," Journal of Analytical and Applied Pyrolysis 66, pp. 29-50 (2003).
Sarotti et al., "An Efficient Microwave-Assisted Green Transformation of Cellulose into Levoglucosenone. Advantages of the Use of an Experimental Design Approach," Green Chem., vol. 9, pp. 1137-1140 (2007).
Shafizadeh and Fu, "Pyrolysis of Cellulose," Carbohydrate Research 29, pp. 133-122 (1973).
Shafizadeh and Stevenson, "Saccharification of Douglas-Fir Wood by a Combination of Prehydrolysis and Pyrolysis," Journal of Applied Polymer Science, 27, pp. 4577-4585 (1982).
Shafizadeh et al., "Acid-Catalyzed Pyrolyctic Synthesis and Decomposition of 1,4:3-6-Dianhydro-X-D-Glucopyranose," Carbohydrate Research 61, pp. 519-528 (1978).
Shafizadeh et al., "Preparation of 1,6-Anhydro-3,4-Dideoxy-β-D-glycero-Hex-3-Enopyranos-2-Ulose (Levoglucosenone) and Some Derivatives Thereof," Carbohydrate Research 58, pp. 79-87 (1977).
Shafizadeh et al., "Production of Levoglucosan and Glucose from Pyrolysis of Cellulosic Materials," Journal of Applied Polymer Science 23, pp. 3525-3539 (1979).
Shafizadeh et al., "Some Reactions of Levoglucosenone," Carbohydrate Research, 71, pp. 169-191 (1979).
Shafizadeh, "Introduction to Pyrolysis of Biomass," Journal of Analytical and Applied Pyrolysis 3, pp. 283-305 (1982).
Sheldrake and Schleck, "Dicationic Molten Salts (Ionic Liquids) as Re-usable Media for the Controlled Pyrolysis of Cellulose to Anhydrosugars," Green Chem., vol. 9, pp. 1044-1046 (2007).
Shen and Gu, "The Mechanism for Thermal Decomposition of Cellulose and its Main Products," Bioresource Technology 100, pp. 6496-6504 (2009).
Shen et al., "Study on the Pyrolytic Behaviour of Xylan-based Hemicellulose Using TG-FTIR and Py-GC-FTIR," Journal of Analytical and Applied Pyrolysis 87, pp. 199-206 (2010).
Suarez, "Recycling of waste paper for obtaining high value added products," First report, PICTO 2005-2006, Organic Letters (2006).
Trahanovsky et al., "A Convenient Procedure for the Preparation of Levoglucosenone from Cellulose and the Conversion of Levoglucosenone to Novel Chiral Derivatives," pp. 228-230 (2003).
Witczak, "Levoglucosenon: A Chiral Building Block with a New Persepctive," American Chemical Society, pp. 81-97 (2001).
Witczak, "New Stereoselective Functionalization of Cellulose-Derived Pyrolysis Derivatives: Levoglucosenone and Its Dimer," American Chemical Society, pp. 332-345(2007).
Yang et al., "Studies on Pyrolysis of Wheat Straw Residues From Ethanol Production by Solid-State Fermentation," Journal of Analytical and Applied Pyrolysis 81, pp. 243-246 (2008).
Yanik et al., "Fast Pyrolysis of Agricultural Wastes: Characterization of Pyrolysis Products," Fuel Processing Technology 88, pp. 942-947 (2007).
Halpern, Y., Riffer, R. and Briodo, A., Journal of Organic Chemistry, (1973), vol. 38, No. 2, pp. 204-209.
Shafizadeh, F., Furneaux, R. H. and Stevenson, T. T., Carbohydrate Research, (1979), vol. 71, pp. 161-191.

\* cited by examiner

METHOD FOR CONVERTING LIGNOCELLULOSIC MATERIALS INTO USEFUL CHEMICALS

This application is a 35 USC §371 national phase entry of PCT/AU2010/000811, which is incorporated herein as if fully set forth.

FIELD OF THE INVENTION

The invention relates to a method of thermochemical treatment of lignocellulosic materials so that they are converted to a mixture of volatile organic compounds, water and char.

BACKGROUND OF THE INVENTION

In this specification, where a document, act or item of knowledge is referred to or discussed, this reference or discussion is not an admission that the document, act or item of knowledge or any combination thereof was at the priority date:
  (i) part of common general knowledge; or
  (ii) known to be relevant to an attempt to solve any problem with which this specification is concerned.

The great majority of synthetic organic chemicals, including polymers, pharmaceuticals, herbicides, pesticides, dyes, pigments, and liquid transport fuels are derived from crude petroleum from fossil sources. The reserves of crude petroleum are limited and the majority are located in politically unstable regions of the world. Furthermore, the combustion of petroleum-derived fuels in internal combustion engines has been shown to be a major contributor to the anthropogenic gaseous emissions into the atmosphere (so-called "greenhouse gases") that have been demonstrated to be the major cause of global climate change. The International Panel on Climate Change (IPCC) has recommended that all nations work towards reducing emissions of greenhouse gases as soon as possible.

One of the recommended means of reducing emission of greenhouse gases is full, or partial, replacement of petroleum-derived organic compounds such as transport fuels with organic compounds derived from renewable resources, such as plantation forestry, agriculture and aquaculture. This replacement would have the additional advantage of reducing the rate of usage of the limited remaining fossil petroleum reserves and permit their exploitation to be restricted to production of synthetic organic chemicals that cannot be made cost-effectively from renewable resources. With the exception of limited annual supplies of vegetable oils and fats, high volume renewable organic materials that can be harvested in a cost effective manner are generally non-volatile solids. The overwhelming majority of existing internal combustion engines require their fuels to be either volatile organic liquids under ambient pressures and temperatures, or gases that can be condensed into liquids under moderately increased pressures, such as propane and butane.

Many means of converting renewable solid organic materials, into organic liquids, especially volatile, energy-dense organic liquids using thermochemical processing, biochemical processing and/or biological processing, are being actively developed worldwide. The existing means generally have significant disadvantages, especially in relation to the production of useful liquid fuels that are compatible with existing internal combustion engines. These disadvantages include the use of expensive enzymes, the requirement for processing at high pressures, necessitating the use of very large processing facilities with associated high costs associated with transporting bulky renewable organic materials over large collection areas, low net yields of energy, chemical complexity and instability of the liquid products and additional demands for often scarce resources of fresh water.

Thus there is a need to develop means for enabling the most abundant, easily collectible renewable organic materials, namely so called "lignocellulosic materials", to be converted selectively into organic liquids without the use of high pressure processing and without the need for large volumes of fresh water. Such organic liquids may either be used directly as fuels, or may be subjected to further processing into renewable liquid fuels, polymers, and other organic chemicals using the prior art.

The term "lignocellulosic material" and forms of the term "lignocellulosic material" as used in this description refers to any vegetable matter, wood, or wood product, paper, paperboard, or paper product, yarn, textile, or textile product having a combined cellulose and hemicellulose content above 30% which can act as a raw material for the invention herein described, and includes but is not limited to cellulose fibre, or cellulose powder, woodchips, sawdust, twigs, bark, leaves, seed pods and other forest litter, cereal and grass straws and hays, oilseed straws, sugar cane bagasse, banana pseudostem waste, oil palm waste, general garden waste, algal "cake" derived from aquaculture and other vegetable matter.

DISCLOSURE OF THE INVENTION

The invention provides in one aspect a method of converting particulate lignocellulosic material to produce volatile organic compounds and char, comprising,
  forming a mixture of the particulate lignocellulosic material with a catalyst composition containing polar organic liquid and an acid,
  heating the mixture to a temperature sufficiently high and for a period sufficiently long as to convert a major portion of any remaining solid phase of the mixture to char whilst agitating the mixture, and
  separating the volatile organic compounds and the catalyst composition as a gaseous phase from the solid phase.

Suitably, the mixture is reacted under sub atmospheric pressure. The pressure may be less than 900 millibar. It may fall within the range 0.1-900 millibar. The pressure may suitably range from 50-150 millibar.

The temperature of the mixture may be raised to a level sufficient to vaporize the catalyst composition during conversion of the solid phase to char.

Suitably, the mixture is heated to a temperature in the range 190° C. to 500° C. The temperature may vary over the period the mixture is heated.

Where the mixture is reacted in a continuously charged reactor such as a rotating screw reactor, the temperature may be controlled along the reactor's length such that the temperature increases from a lower temperature closer to the inlet of the reactor to a higher temperature closer to the outlet.

Suitably, the acid comprises 0.1 to 10% by weight of the catalyst composition.

The weight of the catalyst composition in the mixture may comprise 1 to 10 times the weight of the particulate lignocellulosic material in the mixture.

Prior to being reacted lignocellulosic material in the mixture may be subjected to shearing and compression by any one or more of mechanical defibrators, mechanical or thermomechanical pulping devices, single or twin screw presses, rolling mills, crushing mills, shredding mills and hammer mills.

According to one particular form of the invention there is provided a method of converting a lignocellulosic material, such as cellulosic bleached wood pulp, into a mixture of the volatile organic liquids, (1S)-6,8-dioxabicyclo[3.2.1]oct-2-en-4-one ((−)levoglucosenone), 2-furaldehyde (furfural) and 4-ketopentanoic acid (levulinic acid) by, (a) Suspending the bleached wood pulp in a mixture of a polar organic liquid, that causes the lignocellulose to swell, 0.1-90% by weight of water and 0.1-10% by weight of a strong acid;
(b) Heating the suspension of bleached wood pulp in the liquid mixture under reduced pressure in a device that enables the temperature of the suspension to be raised progressively in a highly controlled manner from ambient to above the boiling point of the polar organic liquid, which is in the range of 190-400 degrees centigrade;
(c) Providing a means of maintaining the liquid vapours in the gas phase so that they can be separated easily and efficiently from any solid carbonaceous char that is formed in b).
(d) Providing a means of collecting and storing the carbonaceous char;
(e) Providing a means of cooling the liquid vapours so that they condense into the liquid phase;
(f) Providing a means of collecting and storing the condensed liquid; and
(g) Providing a means of separating and storing the levoglucosenone, furfural, levulinic acid, water and polar organic liquid, and
(h) Providing a means of recycling the recovered polar organic liquid and water and mixing it with a strong acid for treatment of further quantities of bleached wood pulp, or other lignocellulosic materials.

Preferably, but not essentially, step (a) precedes step (b), which precedes step (c), which precedes (d), which precedes step (e), which precedes step (f), which precedes step (g), which precedes step (h).

In another aspect the invention provides an apparatus for converting lignocellulosic materials into volatile organic liquids and char comprising, a comminution and mixing station for comminuting the lignocellulosic material and mixing the lignocellulosic material with a catalyst composition,
a reactor arranged to receive mixture from the comminution station through an inlet and to discharge char from an outlet located downstream of the inlet,
an evacuation pump arranged to reduce pressure in the reactor,
a feed assembly arranged to move the mixture from the inlet to the outlet so as to discharge char from the outlet,
a heating assembly for heating the mixture in the reactor to a temperature at which pyrolysis of the mixture occurs as it travels through the reactor and
a volatiles condensation assembly for recovering volatiles from the reactor.

The volatiles may comprise volatile organic liquids including chemical products of the conversion reaction, water and catalyst.

Suitably the reactor has an elongate tubular section and the feed assembly comprises a screw feeder within the tubular section.

A steam assembly may be arranged to inject steam into the reactor at at least one location downstream of the inlet.

Also a gas-solid separation system and a fractional distillation system may be located downstream of the outlet.

The invention will now be further explained by reference to the following example which illustrates a specific method and apparatus for performing the invention.

EXAMPLE 1

Example 1 given here is generally directed to treatment of cellulosic bleached wood pulp but, as will be apparent to one skilled in the art, most of the methods are equally applicable to other lignocellulosic materials, such as cellulose fibre, cellulose powder, waste paper, woodchips, sawdust, twigs, bark, leaves and other forest litter, cereal and grass straws and hays, oilseed straws, sugar cane bagasse, banana pseudostem waste, oil palm waste, garden waste, algal "cake" derived from aquaculture or any vegetable material having a significant content of cellulose and/or hemicellulose.

Cellulosic bleached wood pulp is put through a shredder, or some other means of comminuting the wood pulp into strips, or pieces no greater than 1 cm thick, but preferably in the range 3-6 mm thick. The comminuted wood pulp is sprayed with a mixture of a high boiling polar organic liquid and a strong acid. The organic liquid can be chosen from any polar organic liquid that swells cellulose and is thermally and chemically stable at a temperature of 300 degrees centigrade and is desirably non-toxic, or low toxicity. The organic liquid may be chosen from polar organic liquids such as room temperature ionic liquids having the general formula $A_xM_y$, where A is an organic cation, such as dialkyl imidazolium or alkyl pyridinium and M is an anion drawn from typical halide, or sulfate anions, or organic anions, such as formate, acetate, trifluoromethanesulfonate ("triflate"), or bis(trifluoromethane)sulfonimide ("bistriflimide") and where x and y are integers, such that the overall electronic charge of the formula is zero, or dipolar aprotic liquids such as dialkylformamides, N-alkyl morpholine oxides, dialkyl sulfoxides, or dialkyl sulfones having the one general chemical formal $R_1$—$SO_2$—$R_2$ where $R_1$ and $R_2$ are alkyl groups containing between one and ten carbon atoms, including cyclic sulfones in which $R_1$ and $R_2$ form part of a cyclic polymethylene ring. Preferentially the organic liquid is tetramethylene sulfone ("sulfolane") and the strong acid with which it has been mixed is orthophosphoric acid added in amounts between 0.1-10%, but preferentially between 2-3% of the weight of the sulfolane. The mixture of sulfolane and acid is heated to a temperature between 50-200 degrees, but preferentially in the range 150-170 degrees prior to spraying on to the wood pulp to accelerate penetration and swelling of the cellulose. Other strong acids, such as sulfuric acid, methanesulfonic acid, trifluoromethanesulfonic acid ("triflic acid") hydrohalic acids, nitric acid and formic acid may also be employed, but orthophosphoric acid is preferred in cases where the carbonaceous char is to be used as an agricultural or horticultural fertilizer and a carbon sequestering agent. As a second step, hot water at a temperature between 50-100 degrees but preferentially in the range 90-100 degrees may be sprayed onto the wood pulp at rates between 0.1-5 times the rate of sulfolane used but preferentially in the range 0.5-1 times the rate of sulfolane used. The organic liquid and water mixed with strong acid ("swelling catalyst") is sprayed onto the bleached wood pulp at rates between 100-1000% of the mass of pulp being processed, but preferentially at a rate between 150-350% of the mass of pulp. For other lignocellulosic materials, the proportion of swelling catalyst used should be adjusted so that sufficient is added to swell most the cellulose and hemicellulose present so that the acid can penetrate the material rapidly.

The mixture of wood pulp and swelling catalyst is next passed into a means of applying strong shearing and compressing forces that assist in ensuring the swelling catalyst is as evenly distributed throughout the lignocellulosic material as possible. Such means include mechanical defibrators, mechanical or thermomechanical pulping devices, single or twin-screw presses, rolling mills, crushing mills, shredding mills and hammer mills, but preferentially a crushing mill such as is used for crushing sugar cane.

The crushed mixture of pulp and swelling catalyst is then fed via a plug screw into the inlet of an auger reactor in which a single screw, or twin screws may be employed, but preferentially counter-rotating twin screws. The outlet of the auger reactor is fitted with a means of separating gaseous reaction products from solid reaction products under reduced pressure, such as a series of heated cyclones, that are connected in turn to an efficient fractional distillation column. The outlet of the auger reactor, the cyclones and the fractional distillation column are connected to a means of applying a reduced pressure between 0.1 and 500 millibar, but preferentially in the range 50-150 millibar. The auger reactor is equipped with a means of applying heat in a controlled manner to the barrel of the screws such that the mixture of swelling catalyst and wood pulp is heated quickly to a temperature of 180 degrees centigrade at the inlet end and then in a controlled manner to a temperature between 220 and 500 degrees centigrade, but preferentially in the range 380-450 degrees centigrade as it is moved along the length of the reactor under the action of the screws. The residence time of the mixture in the auger reactor may be in the range 1-60 minutes, but preferentially in the range 1-5 minutes.

The action of heat and the acid on the swollen wood pulp during its period in the auger reactor causes dehydration of the anhydrohexose and anhydropentose residues from which the cellulose and hemicelluloses present are made up, resulting in formation of levoglucosenone as the major volatile product in molar yields of 10-40% with smaller amounts of water, furfural, levulinic acid, 5-hydroxymethylfurfural, acetic acid and formic acid. Significant quantities of non-volatile carbonaceous char are also formed by dehydration of the lignin present in the pulp and also, presumably, by further reaction and thermal decomposition of some of the volatile products. The residence time and rate of heating must be kept under careful control in order to minimize the undesirable loss of volatile products via the latter mechanism. Under the reduced pressured in the auger reactor the water, sulfolane, levoglucosenone, furfural and other volatile products boil rapidly and the pressure of these vapours assists in agitating unreacted pulp and in carrying the carbonaceous char through the outlet of the auger reactor. The pressure differential created by the boiling water, sulfolane and volatile dehydration products cause the vapours to be conveyed rapidly along the auger reactor, through the outlet and into the cyclone. If the walls of the cyclone are held at a temperature between 200 and 250 degrees centigrade, under reduced pressure all of the volatile products remain in the vapour phase and separation from the solid carbonaceous char is efficient and complete. The carbonaceous char may be preferentially allowed to fall onto the surface of a heat exchanger carrying swelling catalyst to the sprays, so that the bleached wood pulp is sprayed with hot swelling catalyst. After cooling the carbonaceous char can be conveyed to a storage vessel, where part of it can be fed to a gasifier to provide fuel gas that can be used to heat and maintain the temperature of the barrel of the auger reactor. The unused part of the carbonaceous char may be used as a renewable fuel, or it may be used as an agricultural or horticultural fertilizer, in which use it also acts as a means of sequestering carbon in the soil.

The vapours of the water, sulfolane and the volatile chemical dehydration products pass through a cyclone and into the base of the distillation vessel fitted with an efficient fractional distillation column held under a reduced pressure in the range 1-300 millibar, but preferentially in the range 90-110 millibar. Under these conditions progressive controlled heating and cooling of the distillation vessel provides efficient separation of water, formic acid, acetic acid, furfural, levoglucosenone and sulfolane which may be in purities above 90%. The water, formic acid, acetic acid, furfural and levoglucosenone are collected and pumped to separate storage tanks for sale and distribution. If renewable liquid fuels are sought, both levoglucosenone and furfural may be converted to ethyl levulinate, 2-methyltetrahydrofuran (MTHF) and other volatile liquid fuels using methods known in the art.

The minor volatile products, including levulinic acid and hydroxymethylfurfural are combined with the recovered sulfolane. Still bottoms, that include humic substances commonly referred to as "humins" and tarry substances, are combined with the proportion of char that is fed to the gasifier.

EXAMPLE 2

Example 2 given here illustrates the versatility of the apparatus and the process in that it is very similar to Example 1 above, save that no orthophosphoric acid is included in the catalyst, but sulfuric acid is added in its place in amounts between 0.1-5%, but preferentially in the range 2-4%. In this case, if wood pulp, or other cellulosic or lignocellulosic material is mixed with the catalyst as described in Example 1 and the mixture is processed as described in Example 1, the major volatile organic product is 5-ketopentanoic acid (levulinic acid) accompanied by smaller amounts of levoglucosenone that can be separated using fractional vacuum distillation.

Figure 2:
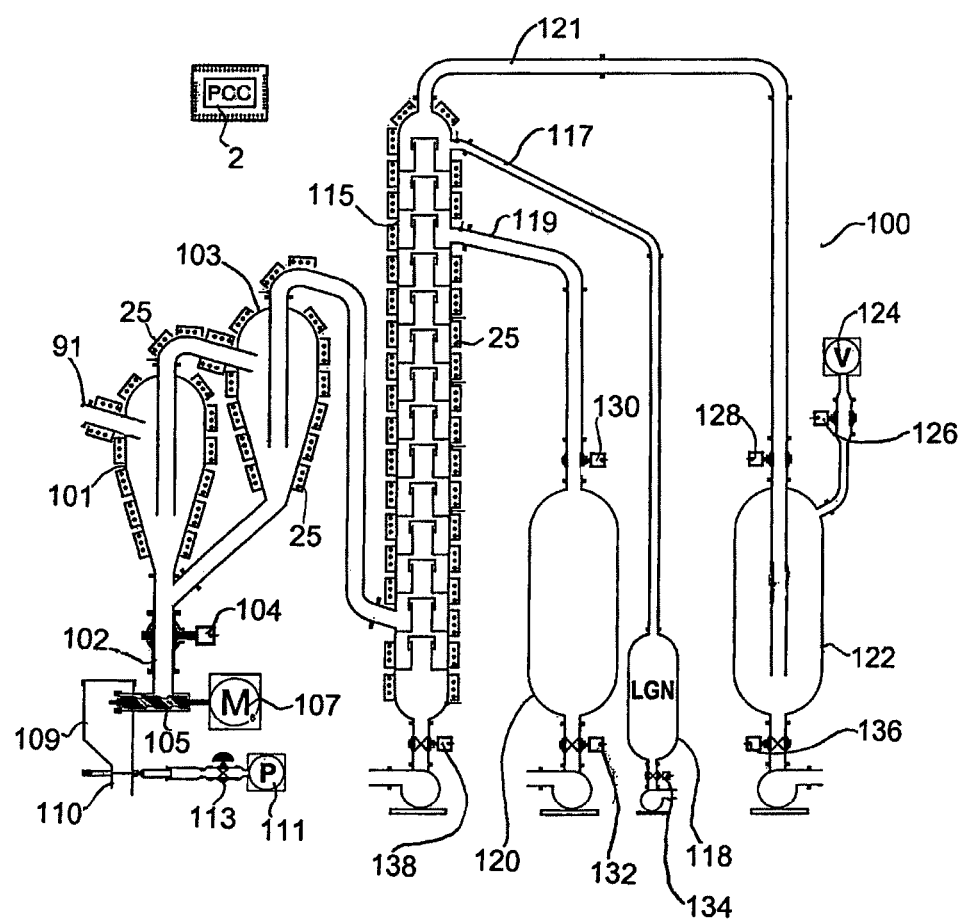
Figure 3:
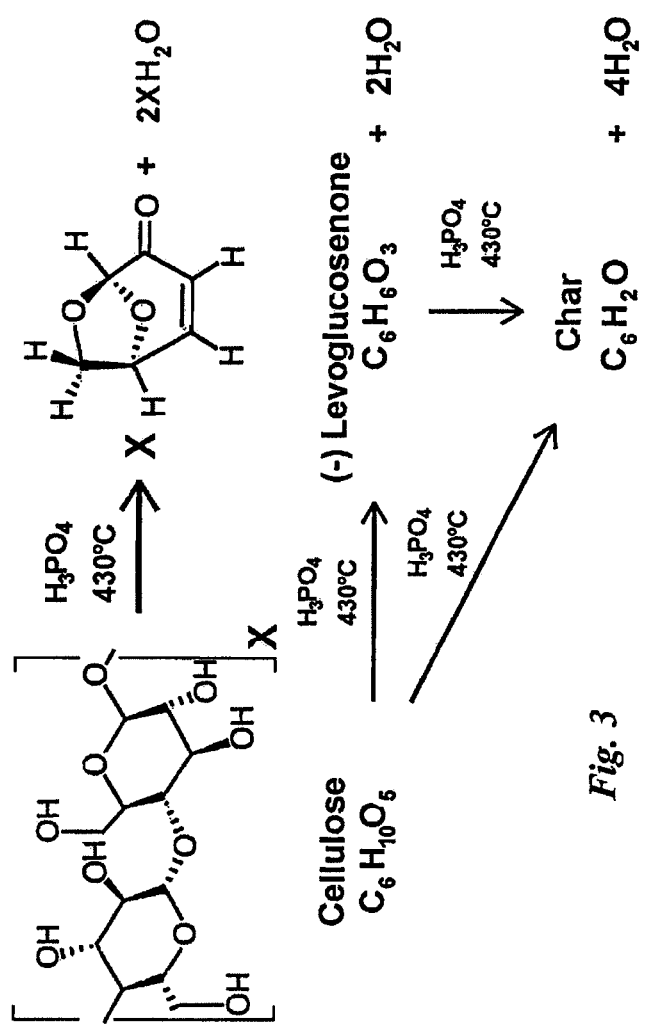

Aspects of an apparatus for performing the invention and specific conditions for operating the apparatus will now be described with reference to the accompanying drawings wherein FIG. 1 is a diagrammatic view of a pyrolysis portion of an apparatus according to the invention;

FIG. 2 is a diagrammatic view of a separation/distillation system to be used in conjunction with the apparatus of FIG. 1; and FIG. 3 shows an abbreviated equation of the reaction pathway according to the present invention.

The various elements identified by numerals in the drawings are listed in the following integer list.

INTEGER LIST

1 Pyrolysis apparatus
2 Process control computer
3 Feed chute
5 Solids/catalyst mixture
7 Feed screw
9 Motor
11 Feed tank
13 Agitator attached to positive thrust screw 15 Motor
17 Fluid plug
19 Valve
21 Screw reactor
22 Feed screw
23 Motor
25 Heater
27 Inspection port
29 Camera
31 Transparent cover
33 Steam source
35 Steam purge line
37 Steam purge line
39 Steam purge line
41 Steam purge line
43 Valve
45 Valve
47 Valve
49 Valve
51 Hurdle
53 Hurdle
55 Drive shaft
57 Motor
58 Gearbox
59 Scraper bar
61 Scraper bar
62 Outlet wall
63 Char
65 Char vessel
67 Valve
69 Vacuum source
71 Pelletising press
73 Motor
74 Pellets
75 Pellet vessel
77 Nitrogen source
79 Valve
81 Valve
83 Valve
85 Pneumatic fluid source
87 Valve
89 Outlet
91 Volatiles outlet conduit
100 Separation/distillation complex
101 Cyclone
102 Outlet
103 Cyclone
104 Valve
105 Char press
107 Motor
109 Pellet hopper
110 Outlet
111 Pneumatic source
113 Valve
115 Vacuum fractional distillation column
117 Take off point
118 Storage vessel
119 Take off point
120 Storage vessel
121 Take off point
122 Storage vessel
124 Vacuum source
126 Valve
128 Valve
130 Valve
132 Valve
134 Valve
136 Valve
138 Valve

DETAILED DESCRIPTION OF FIGS. 1 AND 2 OF THE DRAWINGS

Referring to FIG. 1 of the drawings, there is shown a pyrolysis apparatus generally designated 1 which is controlled by a process control computer 2.

The apparatus has a feed chute 3 arranged to deliver a solids/catalyst mixture 5 to a feed screw 7.

The feed screw 7 which is driven by motor 9 is arranged to direct feed into the feed tank 11.

An agitator 13 attached to a positive thrust screw driven by motor 15 is provided in the feed tank for mixing the feed. The feed forms a fluid plug 17 at the bottom of the feed tank.

A valve 19 which is operated by the process control computer 2 controls the delivery of the mixture to the screw reactor 21.

The feed screw 22 of the screw reactor is driven by the motor 23.

The tubular walls of the reactor are surrounded by a series of electric heaters 25 arranged annually around the screw reactor. The heaters may be also controlled by the process control computer 2.

An inspection port 27 is located at an intermediate position along the length of the screw reactor 21. It includes a transparent cover 31 above which a camera 29 may be mounted.

Steam purge lines 35, 37, 39 and 41 supplied by the steam source 33 are provided at various positions along the length of the screw reactor. The valves 43, 44, 47 and 49 which are also controlled by the process control 2, are arranged to control delivery of steam through the purge lines to the screw reactor.

In the case where a reactor containing a single screw is used, hurdles 51 and 53 are provided at various points within the reactor for purposes to become apparent.

The end of the screw reactor is provided with an outlet defined by the outlet walls 62 through which the char 63 falls.

A rod 55 provided with scraper bars 59 and 61 extends through the tubular outlet and is driven by a motor 57 acting through the gearbox 58.

A char vessel 65 communicates with the outlet and is arranged to receive char falling into the outlet.

A vacuum source 69 regulated by the valve 67 is provided to ensure that the char vessel and screw reactor 21 are maintained at reduced pressure. It is noted that the char vessel 65 and outlet walls 62 are also provided with heaters 25 for maintaining temperatures within desired ranges.

A pelletising press 71 driven by the motor 73 is arranged to compress char filled in the char vessel and to drop pellets 74 into the pellet vessel 75.

Both the char vessel 65 and pellet vessel 75 communicate with a nitrogen source 77 controlled by the valves 81 and 79 respectively.

Similarly, the outlet wall 62 of the outlet also communicates with the nitrogen source 77 through the valve 83. Suitably valves 83 and 79 are controlled by the process control computer 2 whereas valves 67 and 81 may be manually operable.

The bottom of the pellet vessel terminating in the outlet 89 communicates with a pneumatic fluid source 85 through the manually operable valve 87.

The volatiles outlet conduit 91 communicates with the separation/distillation complex 100 now described with reference to FIG. 2.

The conduit 91 communicates with the cyclone 101 which in turn is in communication with the cyclone 103 in series.

Both cyclones 101 and 103 jointly have an outlet 102 for solid material separated by the cyclones.

A valve 104 operated by the process control computer 2 can be used to regulate the flow of fines into the char press 105 driven by the motor 107.

A pellet hopper 109 is arranged to receive pellets from the char press and the outlet 110 of the pellet hopper is provided with a pneumatic source 111 controlled by the manually operable valve 113.

The cyclone 103 is in communication with the vacuum fractional distillation column 115. Both the cyclones 101 and 103 as well as the vacuum fractional distillation column are provided with heaters 25 controlled by the process control computer 2.

The fractional distillation column has take off points 117, 119 and 121 which lead to storage vessels 118, 120 and 122 respectively.

The storage vessel 122 is in communication with a vacuum source 124 via the valve 126. Similarly valves 128 and 130 can be used to regulate flow of volatiles into the storage vessels as well as pressure in the assembly.

Valves 132, 134 and 136 provided at the outlets of the storage vessels, as well as valve 138 at the outlet of the fractional distillation column allow for regulated removal of condensed volatiles from the column or storage vessels.

Process Summary

FIG. 3 shows in brief outline some of the chemical equations involved in operating the process of the invention using the apparatus described with reference to FIGS. 1 and 2. The reaction can take place in a continuous manner with reaction products being formed rapidly and extracted using a solids/vapours/liquids series of separations steps.

Beginning with the apparatus of FIG. 1 a mixture of the solid lignocellulosic material and a liquid catalyst, "the mixture", is allowed to fall into the feed opening 3 of the first rotating feed screw. If necessary, the solid lignocellulosic material is suitably reduced to a particulate form at a comminution station upstream of the feed opening.

The screw 7 is arranged such that mixture 5 is fed into the inlet of the feed tank 11. The screw may itself act to comminute the solid lignocellulosic material into smaller particulate form.

The feed tank 11 is equipped with a means of agitation and a positive thrust screw 13 such that the mixture is forced by positive pressure from the screw to form a fluid plug inside the feed tank.

The fluid plug of mixture is forced by a combination of air pressure and the thrust from the screw through an open valve 19 into the inlet of a rotating screw reactor 21. The positive thrust screw is driven through a gearbox 58 by motor 15 that also enables the thrust screw to be raised above the valve 19 at times when the valve 19 needs to be closed at the beginning, or the end of a processing run.

The screw reactor may be either of a single screw type, or a twin screw type. It is driven by a variable speed motor 23 controlled by computer 2 in such a way that it moves the mixture from the inlet of the reactor into the beginning of the heated zone where the heaters 25 begin.

The beginning of the heated zone of the reactor is suitably maintained at a temperature within a 10 degree range that is dependent on the vapour pressure of the particular liquid catalyst that is used. The mean temperature can be in the range 0-250° C., but is preferentially in the range 170-180° C. when the catalyst comprises a mixture of orthophosphoric acid, water and tetramethylene sulfone (sulfolane).

The inside of the reactor is maintained at an absolute pressure in the range 0.1-900 millibar through the connection of a vacuum pump in FIG. 2 downstream of the outlet of the reactor. When the catalyst comprises a mixture of orthophosphoric acid, water and tetramethylene sulfone (sulfolane), the pressure inside the reactor is more preferentially in the range 80-120 millibar.

The pressure and temperature inside the reactor are controlled by a process control computer 2, or manually, such that the catalyst starts boiling rapidly as soon as it reaches the heated zone creating a vapour that is drawn at high speed towards the outlet conduit 91 by the pressure differential that is created by the boiling catalyst.

The kinetic energy of the vapour stream causes the remaining mixture to break into particles in the size range 0.1-10 mm. These are carried at high speed in a predominantly spiral path around the flutes of the screw of the reactor 21. As the particles collide with one another, the wall of the reactor and the flights of the screw, they break apart into smaller and smaller fragments. This process is more efficient when counter-rotating twin screws are used as the particles become caught in the nip between the screws and are broken down in size more rapidly. Simultaneously, vapour is boiling from the surface of the particles causing the remaining lignocellulose to become less and less cohesive and allowing the particles to fragment further such that heat transfer into the particles is very rapid and efficient.

The temperature profile along the screw reactor 21 is controlled using heaters 25. These have an annular geometry and surround the reactor. Thus the reagents reaching a location along the reactor in the vicinity of the inspection port 27 comprise largely a mixture of rapidly moving solid particles of lignocellulose containing residual orthophosphoric acid and some tetramethylene sulfone with sizes in the range 0.1-3 mm and a high speed vapour stream comprising mainly water, tetramethylene sulfone and volatile chemical dehydration products including levoglucosenone.

The sealed inspection port 27 that allows visual, or automated, verification of the composition of the reagents is desirably equipped with steam purges that are capable of keeping the glass cover 31 and the shaft of the port free of solid material that will obscure the view of the moving stream of solid particles and vapour.

A second series of heaters 25 of annular geometry mounted around the periphery of the reactor are provided downstream of the inspection port 27. These are controlled by the process control computer or by manual means, such that the temperature range begins at 300° C.±10° C. rising to 440° C.±10° C. further along in the direction of the outlet of the reactor tube. In the case when a single screw reactor is employed, a series of metal hurdles 51 and 53 are provided between the periphery of the flights of the screw between points. The hurdles are arranged such that the gap through which the vapour stream must pass is reduced in width from about 3 mm to about 1 mm thereby preventing particles of lignocellulose and catalyst that are larger than 1 mm in size from exiting the heated zone. When conditions of temperature, pressure, rotation speeds of the screws and catalyst composition are adjusted correctly it is found that the outer surfaces of the lignocellulose particles are pyrolysed to a mixture of a friable char and a simple mixture of volatile gaseous products that join the vapour stream and exit the heated zone with residence times typically in the range 0.1-1 second. Further, it is found that under appropriate conditions, a combination of the rapidly moving vapour stream with entrained char particles and evolution of volatile products causes continual ablation of the surface layer of char from the lignocellulose particles, exposing fresh lignocellulose and reducing the size of the particles so that they can pass through progressively smaller and smaller gaps. Under these ablative conditions, substantially all of the lignocellulose particles can be reduced in size below 1 mm and are carried out of the heater zone and denser particles fall under gravity into a heated char collection vessel 65.

Because some of the products of pyrolysis cause some of the char to adhere to the surfaces of the screw, the hurdles 51, 53 (if present) and the walls of the reactor, steam purges 35, 37, 39 and 41, that may either be under computer, or manual control, are provided to clean the accumulated char from the surfaces periodically during the operation of the reactor. The frequency and duration of the operation of the steam purges can be varied depending on the form of lignocellulosic material being fed and a practitioner skilled in the art will be able to determine these parameters so that continuous operation of the reactor lasting many days is possible.

Further cleaning of accumulated char from the walls 62 of the outlet of the reactor is provided by a series of scraper bars 59, 61 that are attached to a bar 55 that rotates and reciprocates up and down driven through the gearbox 58 from the motor 57.

Heat is applied through heaters 25 around the walls of the outlet 62, the char vessel 65 and the volatiles conduit 91 to control the temperature such that the vapour of the catalyst, the desired chemical dehydration products in the vapour phase and water vapour do not condense into the liquid phase. Typically temperatures in the range 200-250° C. are maintained.

The fine particles of char falling into the collection vessel 65 may be collected, transported and used directly as a renewable solid fuel, or as a carbon sequestration agent and fertilizer in agricultural and horticultural soils. Optionally the fine particles of char may be subjected to a further screw extrusion process to convert them into char pellets to be collected in the vessel 75. Desirably, when the char is in the form of fine particles, it should be kept under an atmosphere of an inert gas, such as nitrogen from a nitrogen source 77, or carbon dioxide in order to prevent the risk of spontaneous combustion of the char and dust explosions.

Under the conditions described above, the stream of vapours, including water, tetramethylene sulfone and the gaseous products of pyrolysis of the lignocellulosic material together with some entrained, extremely fine solid particles of char flow at high speed out of the reactor through the volatiles outlet conduit 91 and into the gas-solid separation system 100 shown in FIG. 2.

The pressure differential provided by the vacuum source 124 causes the mixture of vapour and solid char to enter a gas-solid separation system comprising two cyclones 101 and 103 shown in series. The walls of the cyclones are maintained at a temperature in the range 150-300° C., but preferentially in the range 260-270° C. by the heaters 25, in order to avoid condensation of any of the vapours in the stream.

Under these conditions typically over 99% of the fine solid char particles are carried by gravity into the collection pipe 102 at the base of the cyclones from where they are fed on automatic level control into a pelletizing press 105 driven by motor 107. The char pellets are collected in a pellet hopper 100 and may be combined with the char pellets stored in the pellet vessel 75.

The remaining vapours, free of char, pass out of the top of the second cyclone 103 and enter the lower zone of an efficient vacuum fractional distillation column 115. The fractional distillation column may be operated batch-wise, or preferentially in continuous mode.

The exterior surface of the distillation column is heated by heaters 25 and cooled by heat exchangers so that a finely controlled temperature gradient is maintained and monitored over the length of the column, ranging from 220-240° C. at the base of the column to 80-90° C. at the top of the column. The position of the heat exchangers is not shown but will be obvious to anyone skilled in the art.

Take-off points 117 and 119 are maintained at 195-200° C. and 180-185° C. respectively at which temperatures a fraction containing 50-60% levoglucosenone can be collected from point 117. A fraction containing about 98% tetramethylene sulfone and less than 2% levoglucosenone can be collected from point 119 and stored in a vessel 120 from where it can be pumped to a tetramethylene sulfone storage vessel.

Vapours passing out of the top of the column at take off point 121 comprise >97% water. These are condensed and collected at vessel 122 from where part of it can be recycled to catalyst preparation, part of it is used for cooling water (cooling water circuits are not shown in the figures as their placement will be obvious to a person skilled in the art) and the excess can be adjusted to neutral pH and sold for crop irrigation and into other markets for non-potable water.

The concentrated solution containing 50-60% levoglucosenone and 40-50% tetramethylene sulfone, called raw LGN, is collected in a vessel 118 from where it can be pumped and purified further.

Whilst the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

The reference to any prior art in this specification is not, and should not be taken as, an acknowledgment or any form of suggestion that such prior art forms part of the common general knowledge in Australia.

The invention claimed is:

1. A method of converting particulate lignocellulosic material to produce levoglucosenone and char, comprising the steps of:
   forming a mixture of the particulate lignocellulosic material with a catalyst composition containing a polar organic liquid and an acid,
   heating the mixture to convert a major portion of a solid phase of the mixture to char and to vaporize a volatile fraction of the catalyst composition during the conversion of the solid phase to char,
   carrying out the heating in a screw reactor under a pressure less than 900 millibar and a temperature in the range of 190° C. to 500° C. while the mixture is subjected to shearing and compression by the screw reactor to produce levoglucosenone,
   injecting steam into the screw reactor during the shearing and compression, and separating the levoglucosenone and the volatile fraction of the catalyst composition as a gaseous phase from the solid phase during the shearing and compression, wherein the polar organic liquid is a room temperature ionic liquid having the general formula $A_xM_y$, where A is an organic cation; M is an anion drawn from halide, sulfate, or organic anions; and x and y are integers, or wherein the polar organic liquid is a dipolar aprotic liquid.

2. The method according to claim 1 wherein A is a dialkyl imidazolium or alkyl pyridinium, and M is a halide, sulfate, formate, acetate, trifluoromethanesulfonate, or bis(trifluoromethane)sulfonimide.

3. The method according to claim 1 wherein the dipolar aprotic liquid comprises a dialkyl formamide, N-alkyl morpholine oxide, dialkyl sulfoxide, or dialkyl sulfone having the general chemical formula $R_1$—$SO_2$—$R_2$ where $R_1$ and $R_2$ are alkyl groups containing between one and ten carbon atoms, including cyclic sulfones in which $R_1$ and $R_2$ form part of a cyclic polymethylene ring.

4. The method according to claim 1 wherein the polar organic liquid comprises tetramethylene sulfone.

5. The method according to claim 1 wherein the acid is chosen from the group consisting of orthophosphoric acid, sulfuric acid, methanesulfonic acid, trifluoromethanesulfonic acid, hydrohalic acids, nitric acid, and formic acid.

6. The method according to claim 1 wherein the acid comprises 0.1% to 10% by weight of the catalyst composition.

7. The method according to claim 1 wherein the weight of the catalyst composition in the mixture is one to ten times the weight of the particulate lignocellulosic material.

8. The method according to claim 1 wherein the mixture is subjected to the shearing and compression by single or twin-screw presses.

9. The method according to claim 1 wherein the screw reactor has an inlet for the mixture and an outlet for the char, and the pressure in the reactor is maintained within the range of 50 to 150 millibar, with the temperature in the reactor being controlled along the reactor's length such that the temperature of the reactor increases from a lower temperature closer to the inlet to a higher temperature closer to the outlet.

* * * * *